(12) United States Patent
Elmaanaoui et al.

(10) Patent No.: US 11,925,430 B2
(45) Date of Patent: *Mar. 12, 2024

(54) PRELOADED STERILE BAG

(71) Applicant: Canon U.S.A., Inc., Melville, NY (US)

(72) Inventors: Badr Elmaanaoui, Belmont, MA (US); Matthew Scott Pias, Brookline, MA (US); Alexander Altshuler, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,724

(22) Filed: Sep. 13, 2022

(65) Prior Publication Data

US 2023/0000581 A1 Jan. 5, 2023

Related U.S. Application Data

(63) Continuation of application No. 16/854,366, filed on Apr. 21, 2020, now Pat. No. 11,471,233.
(Continued)

(51) Int. Cl.
*A61B 46/10* (2016.01)
*A61B 46/23* (2016.01)
*A61B 46/00* (2016.01)

(52) U.S. Cl.
CPC ............. *A61B 46/10* (2016.02); *A61B 46/23* (2016.02); *A61B 2046/234* (2016.02); *A61B 46/40* (2016.02)

(58) Field of Classification Search
CPC ......... A61B 46/10; A61B 46/17; A61B 46/23; A61B 46/40; A61B 2046/205;
(Continued)

(56) References Cited

U.S. PATENT DOCUMENTS

| 5,498,230 A | 3/1996 | Adair |
| 5,876,328 A | 3/1999 | Fox et al. |

(Continued)

FOREIGN PATENT DOCUMENTS

| CN | 106794041 A | 5/2017 |
| JP | H 6-254035 A | 9/1994 |

(Continued)

*Primary Examiner* — Camtu T Nguyen
(74) *Attorney, Agent, or Firm* — Canon U.S.A., Inc., IP Division

(57) ABSTRACT

A sterile bag for covering medical equipment comprises: a barrier section, a flexible body section, and an attaching section. The flexible body section has a tubular shape extending from a proximal end to a distal end thereof, and an outer surface, an inner surface, and an open end. The barrier section is coupled to the proximal end, and the attaching section is formed at the distal end of the flexible body section. The barrier section is a rigid or semirigid component which attaches the sterile bag to a sterile component or to an unsterile component of the medical equipment in a pleaded or folded state. The flexible body section is configured to be deployed over the unsterile component so as to enclose within the inner surface thereof the unsterile component. The unsterile component is connectable to the sterile component through the central opening of the barrier section.

17 Claims, 6 Drawing Sheets

Related U.S. Application Data

(60) Provisional application No. 62/840,932, filed on Apr. 30, 2019.

(58) Field of Classification Search
CPC .... A61B 2046/234; A61B 2017/00367; A61B 2017/00464; A61B 2017/00477; A61B 1/00142; A61B 34/30; A61B 34/35; A61B 34/70; B23Q 11/08; B25J 19/0075; Y10A 90/48; Y10S 901/48
See application file for complete search history.

(56) References Cited

U.S. PATENT DOCUMENTS

| | | | |
|---|---|---|---|
| 7,927,100 B2 * | 4/2011 | Euvrard | A61C 1/16 433/116 |
| 8,459,266 B2 | 6/2013 | Glynn et al. | |
| 10,610,284 B2 | 4/2020 | Hancock et al. | |
| 11,471,233 B2 * | 10/2022 | Elmaanaoui | A61B 46/10 |
| 2002/0133058 A1 | 9/2002 | Calderwood | |
| 2013/0167847 A1 | 7/2013 | Rogers | |
| 2014/0338676 A1 | 11/2014 | Marinchak | |
| 2016/0310224 A1 | 10/2016 | Dye et al. | |
| 2016/0361129 A1 | 12/2016 | Morrissette et al. | |
| 2017/0000361 A1 | 1/2017 | Meyering et al. | |
| 2017/0258544 A1 | 9/2017 | Osman | |
| 2017/0333147 A1 | 11/2017 | Bernstein | |
| 2018/0000472 A1 | 1/2018 | Beira | |
| 2018/0132959 A1 | 5/2018 | Marshall et al. | |
| 2018/0200014 A1 | 7/2018 | Bonny et al. | |
| 2018/0289438 A1 | 10/2018 | Pennoyer | |
| 2021/0220070 A1 | 7/2021 | Okajima et al. | |

FOREIGN PATENT DOCUMENTS

| | | |
|---|---|---|
| JP | H07 204211 A | 8/1995 |
| WO | 2016/012773 A1 | 1/2016 |

* cited by examiner

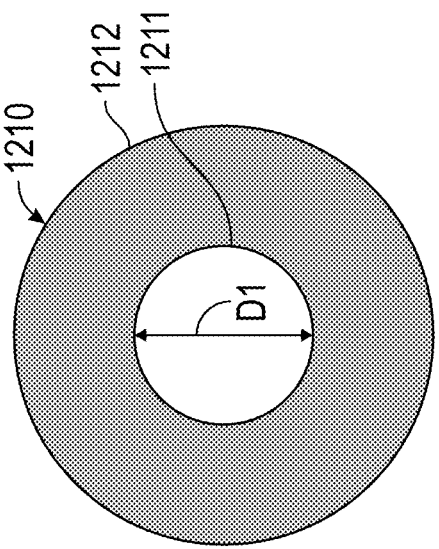
FIG. 3A
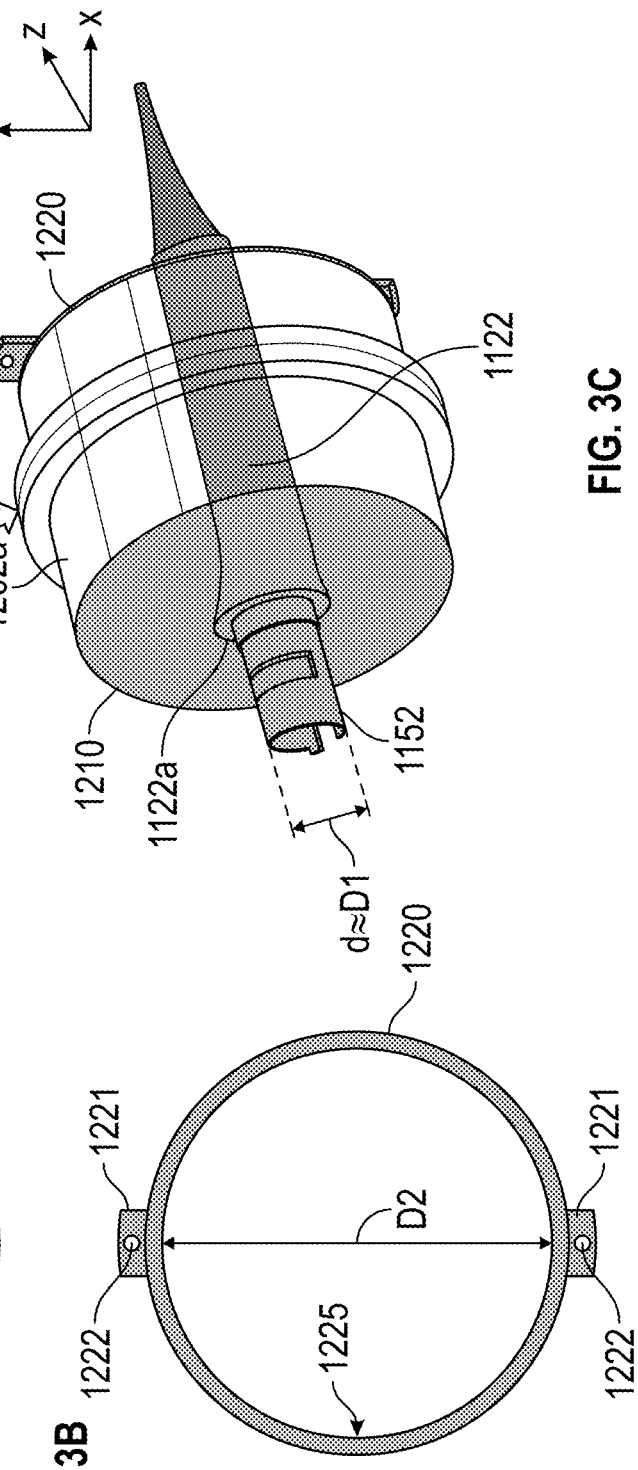
FIG. 3B
FIG. 3C
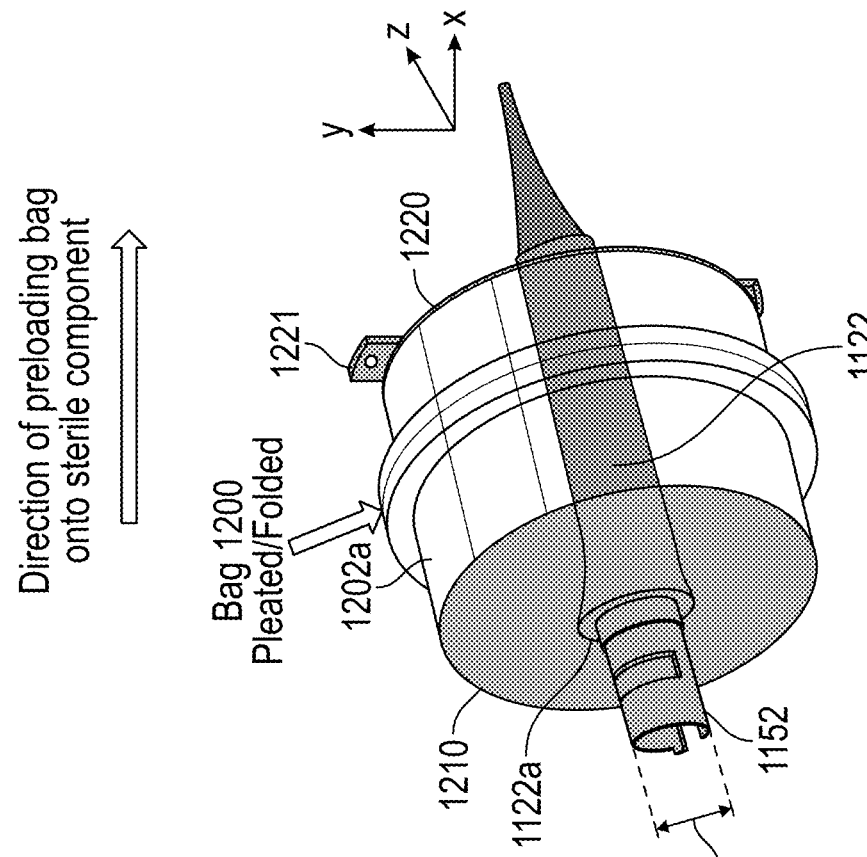

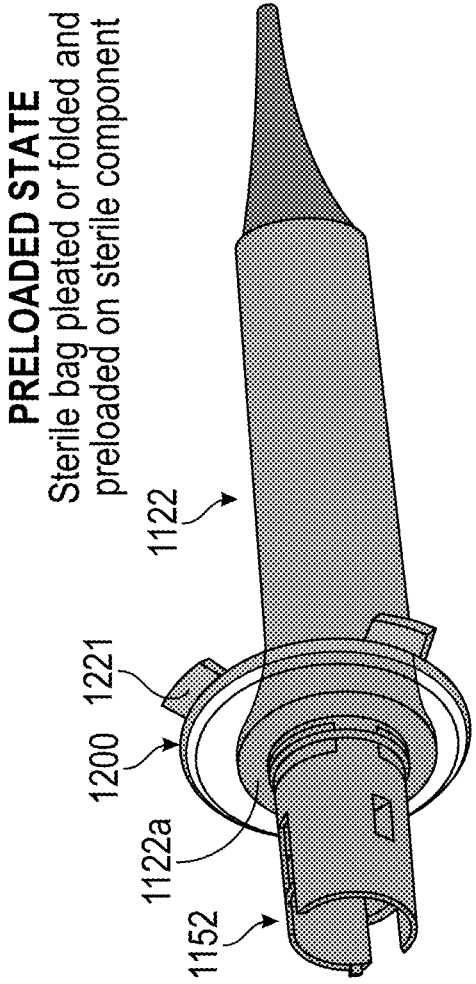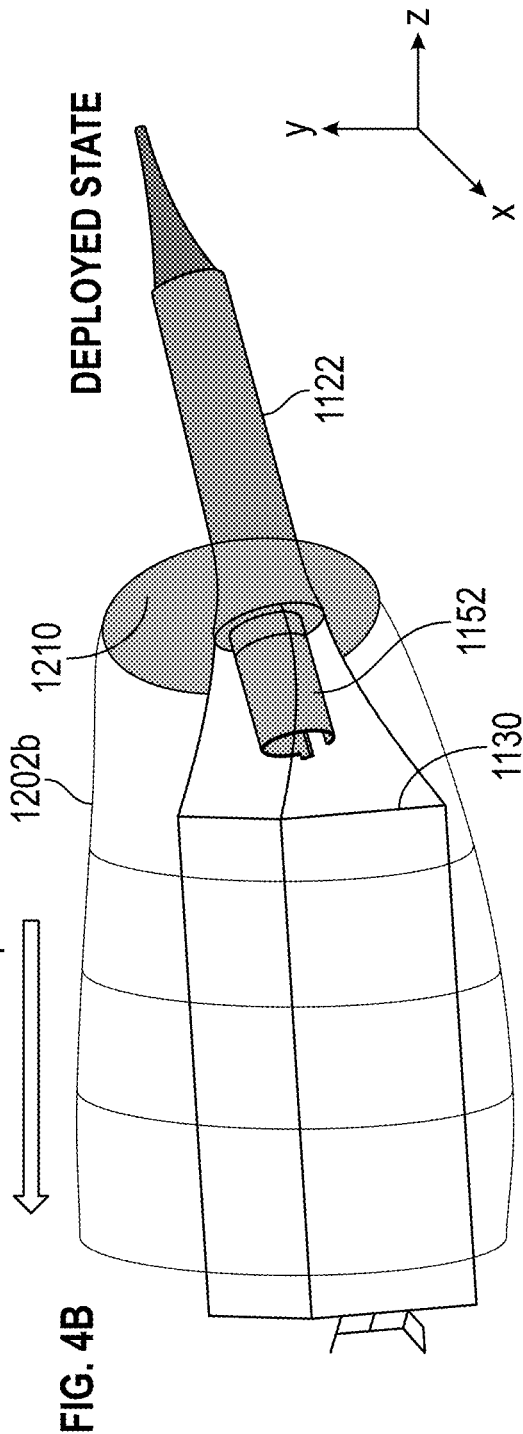
FIG. 4A
FIG. 4B

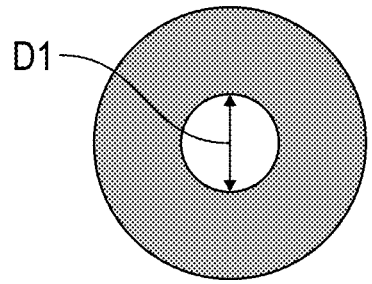
FIG. 5A
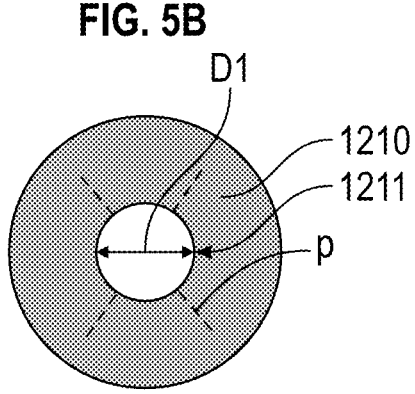
FIG. 5B
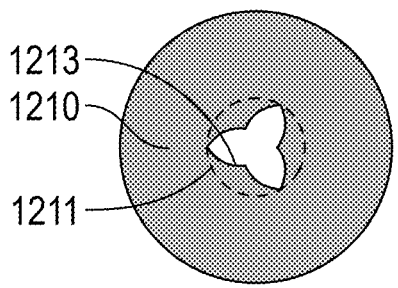
FIG. 5C
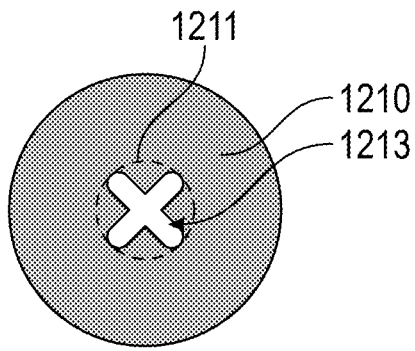
FIG. 5D
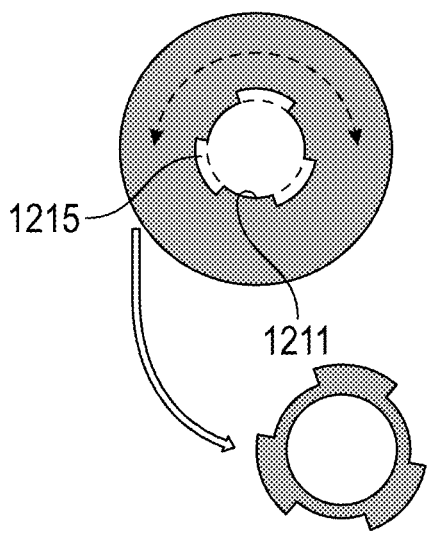
FIG. 5E
FIG. 6A
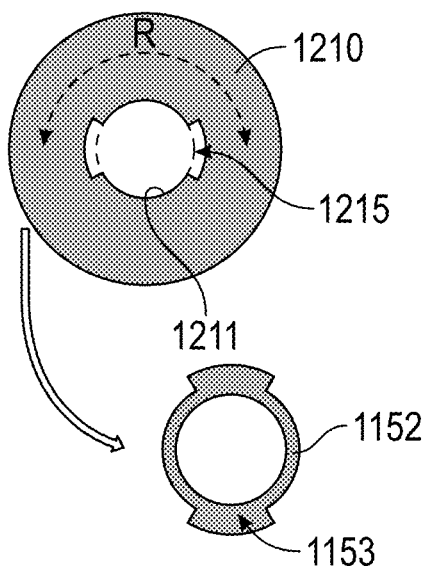
FIG. 5F
FIG. 6B

PRELOADED STERILE BAG

CROSS-REFERENCE TO RELATED APPLICATIONS

The present application is a continuation, and claims the benefit, of U.S. patent application Ser. No. 16/854,366 filed Apr. 21, 2020, which claims priority to U.S. provisional application 62/840,932, filed Apr. 30, 2019. The disclosures of the above-mentioned applications are hereby incorporated by reference herein in their entirety.

BACKGROUND INFORMATION

Field of the Disclosure

The present disclosure relates to medical devices. More particularly, the disclosure exemplifies a sterile bag preloaded onto a sterile medical device and methods of deploying and using the same during interaction of sterile and unsterile medical devices.

Description of Related Art

Sterilization refers to any process that effectively renders any surface, equipment or article free from viable microorganisms. Sterility and its maintenance, together with the prevention of cross-infection, are at the top of any list of critical factors in patient care. In practice, however, it is impossible to prove that all organisms have been destroyed. Therefore Sterility Assurance levels (SAL) are used as a measure of the survival level of microorganisms after terminal sterilization. In Europe, for example, items such as medical devices can only be labelled "sterile" if the chance of an item remaining contaminated after sterilization is less than or equal to one chance in a million. Therefore, the packaging around medical devices is carefully designed so that it allows those devices to be sterilized, provides a microbial barrier and maintains sterility effectively up to the point of use. This type of packaging is known as a sterile barrier system. A sterile barrier system is an essential part of a sterile medical device.

In the medical field, for devices requiring an unsterile and sterile component to interface with each other and pass together into a sterile field, the prior state of the art has primarily relied on a removable sterile cover (e.g., a drape or a bag) that acts as a barrier when deployed over the unsterile component(s). This type of removable cover, in the form of a sterile drape, blanket, or bag, is often rolled or pleated prior to being deployed over the unsterile components to minimize the chance of loss of sterility. To facilitate deployment, tabs are included on the deployment end of the barrier for the user to grip while deploying the barrier. To facilitate attachment, an attached component with a good degree of rigidity or another attachment mechanism may anchor the barrier to the component(s) which the barrier covers. Examples of patent publications related to this type of removable sterile barrier deployable over unsterile components include U.S. Pat. No. 8,459,266 B2 entitled "Pleated bag for interventional pullback systems" and pre-grant patent application publication US 20140338676 A1 entitled "Medical drape and methods of covering equipment with medical drapes". Additional examples of sterile covers are disclosed in pre-grant patent application publications US 20170333147 A1, US 20160361129 A1, and US 20170258544 A1.

For medical systems with the need to cover unsterile components with a sterile bag or drape that interface with sterile components and pass into a sterile field, the bag or drape does not come preloaded to the sterile component. Hence, the use o such barrier requires the user to load a sterile barrier to the sterile/unsterile interface, deploy the bag or drape over the unsterile components, and then load or connect the sterile disposable components to the already covered non-sterile components. This process is time consuming and is prone to accidental loss of sterility when a sterile component comes into contact with an unsterile user or component.

Additionally, in the event that the sterile barrier comes into contact unsterile components, current state of the art lacks the ability to replace a sterile barrier without removing the single-use, sterile, disposable components from the interface. If a mechanism exists to prevent the reuse/reattachment of the sterile components after removal and replacement of the barrier despite the maintenance of sterility of the disposable components, then removal and replacement of the barrier also requires removal and replacement of the disposable sterile component.

Furthermore, current state of the art requires removal of a sterile barrier should the disposable, sterile components need to be removed and/or replaced after barrier deployment, further adding cost and user burden. Moreover, current sterile barrier/drapes lack a method for securing the barrier orifice on the unsterile end so as to prevent the sterile exterior surface of the barrier from coming into contact with unsterile surfaces before passing into the sterile field, hence increasing the likelihood of compromising the sterility of the sterile barrier.

It is evident, therefore, that there is a need for improved sterile barrier/drapes that can provide quick deployment and improved sterility.

SUMMARY OF EXEMPLARY EMBODIMENTS

According to at least one embodiment of the disclosure, there is provided an apparatus comprising a sterile bag preloaded to a disposable sterile component (e.g., catheter handle) in a rolled or folded state; the preloaded sterile bag is configured to be deployed over an unsterile component, where the deployment process takes place in parallel with the engagement of the sterile and unsterile components (e.g., sterile bag deployment occurs in parallel with catheter motor engagement). Upon deployment, a distal end of the sterile bag can be affixed with an attachment to the modality's cart to minimize the possibility of contact with unsterile surfaces or components. The sterile bag can be removable from catheter handle to allow for replacement if the unsterile surface of the bag is contacted by non-sterile components.

In its simplest form, the present disclosure provides a sterile cover for covering medical equipment, comprising: a barrier component configured to be coupled to a sterile component of the medical equipment; and a flexible body coupled to the barrier component, the flexible body having a tubular shape extending from a proximal end to a distal end thereof, and having an outer surface, an inner surface and an open end, wherein the flexible body is configured to enclose within the inner surface a non-sterile component connectable to the sterile component.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 3A, 3B and 3C show various views of an exemplary sterile cover or bag 1200, according to an embodiment of the present disclosure. FIG. 3A shows a plane view of a barrier section 1210, FIG. 3B shows a plane view of an attaching section 1220, and FIG. 3C shows a three-dimensional view of a flexible body section 1202 coupled to the barrier section 1210 and to the attaching section 1220 of the exemplary sterile cover or bag 1200 preloaded onto a sterile component.

FIG. 4A shows an exemplary sterile cover or bag 1200 preloaded onto a sterile component, and FIG. 4B shows an exemplary process of deploying the preloaded sterile cover 1200 over a non-sterile component in parallel with the engagement of the sterile component to non-sterile component.

FIGS. 5A, 5B, 5C, 5D, 5E, and 5F each shows a different design of the barrier section 1210 of the sterile cover or bag 1200, where the barrier section has an opening configured to engage with a connecting portion 1152 of a sterile component.

FIG. 6A illustrates a plane view of an exemplary connecting portion 1152 configured to engage with the barrier section 1210 of FIG. 5E, FIG. 6B illustrates a plane view of an exemplary connecting portion 1152 configured to engage with the barrier section 1210 of FIG. 5F.

Figure 1:
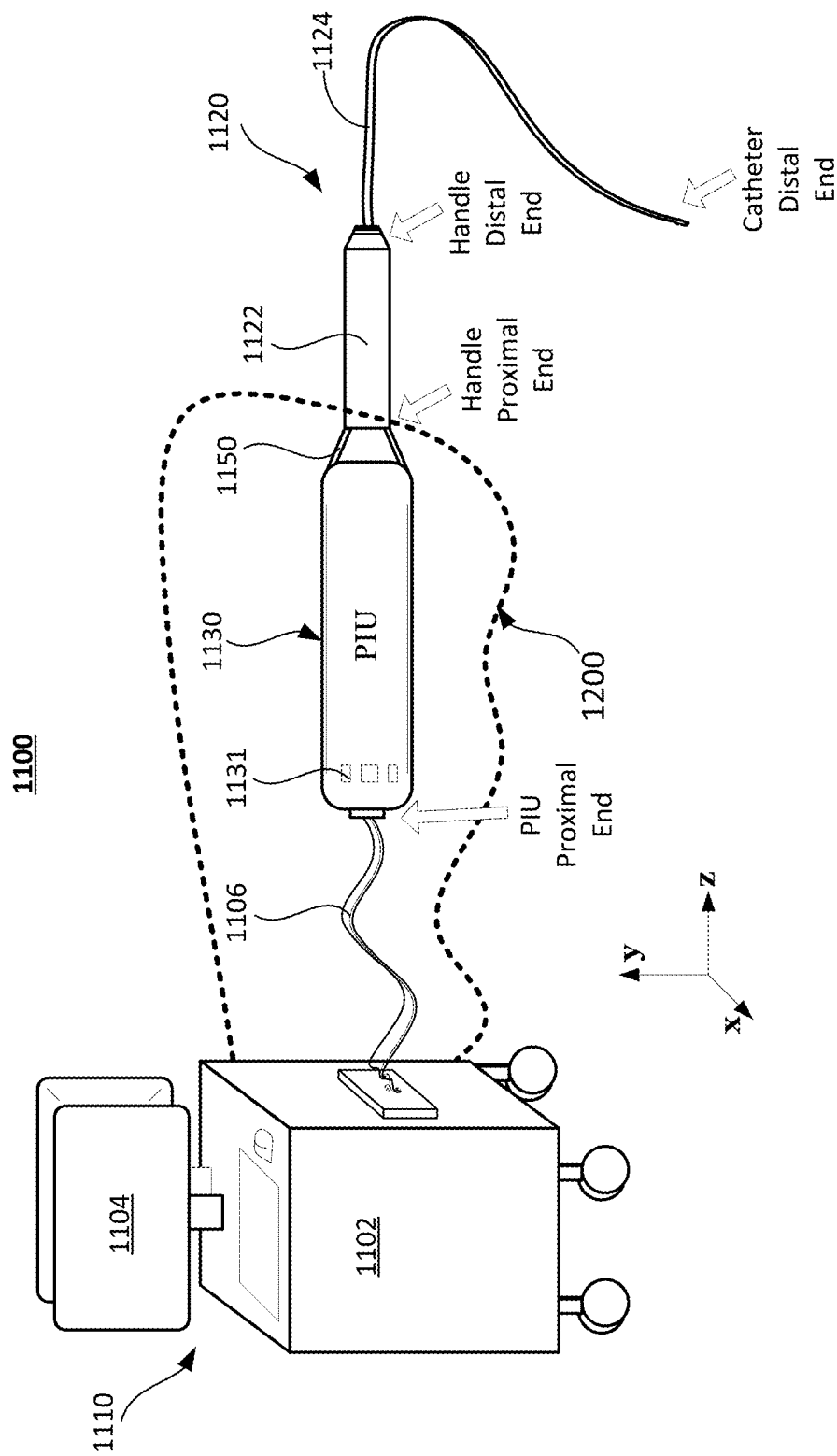
FIG. 1 shows an exemplary medical imaging system where a sterile cover or bag may be implemented.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

DETAILED DESCRIPTION OF EXEMPLARY EMBODIMENTS

The embodiments are based on the object of providing a sterile cover for covering medical equipment which includes sterile and non-sterile components. The sterile cover includes a barrier component configured to be coupled to a sterile component of the medical equipment; and a flexible body coupled to the barrier component, the flexible body having a tubular shape extending from a proximal end to a distal end thereof, and having an outer surface, an inner surface, and an open end. The flexible body is configured to enclose within the inner surface thereof a non-sterile component connectable to the sterile component.

Many medical devices require a sterilized component capable of extending into a sterile field, without risk of contaminating that field, where that sterile component interfaces with an unsterile component needed to operate the device. In this situation, the unsterile component can potentially enter the sterile field and negate the sterility of that filed. A solution to prevent loss of sterility has been to deploy a sterile barrier over any unsterile component entering the sterile field. This especially applies to medical devices used in in-vivo environments, where sterile components such as interventional deployment system catheters must interface with an electronic controller which cannot be sterilized.

Examples of such in-vivo deployable systems include an optical coherence tomography (OCT) catheter system which includes a catheter containing an imaging optical component that interfaces with a pullback system enabling catheter deployment and imaging functionality. The pullback system in turn interfaces with a computer system responsible for the digital operations of the system.

FIG. 1 shows an exemplary medical imaging system 1100. The medical imaging system 1100 includes an imaging console 1110 and a mechanically rotated optical probe 1120 (e.g., an endoscope or catheter). A patient interface unit (PIU) 1130 connects the optical probe 1120 to the imaging console 1110 using a cable bundle 1106. The imaging console 1110 includes, among other things, a computer cart 1102 and one or more displays 1104. The optical probe 1120 may include, for example, a fiber-optic based catheter 1124 and a catheter handle 1122. The handle 1122 has a proximal end and a distal end extending along a z-axis direction. In an exemplary imaging procedure, the imaging system console 1100 controls the catheter 1124 via the PIU 1130 to obtain images of a target sample (not shown), such as a cardiovascular bodily lumen of a patient.

The PIU 1130 is the main interface between the probe 1120 and the system console 1110. The PIU 1130 provides the means to spin and linearly translate the catheter's imaging core within the catheter's stationary outer sheath (not labeled). The system console 1110 and PIU 1130 are connected to each other by the cable bundle 1106. The cable bundle 1106 houses therein cables for transmitting electrical power and for communication signaling, as well as optical fibers for illumination a collection of light. During use of the imaging system console 1100, the entire PIU 1130 is preferably covered with a sterile drape/bag 1200 and placed on the patient's bed or operating table. The PIU 1130 may provide a user interface for operating the imaging functions of the probe from an sterile field by the use of actionable buttons 1131; these buttons 1131 may mirror other controls provided on a graphical user interface (GUI) at the imaging console 1110. The state of each button 1131 (e.g., active, inactive, warning, etc.) is communicated by indicator LEDs provided on the housing of the PIU; and these indicators too are mirrored on the GUI of display 1104. Therefore, users of the medical imaging system 1100 may perform the same operations from either a non-sterile field using the GUI in display 1104 or from the sterile field using the buttons 1131 on the PIU 1130. The PIU 1130 is composed of a beam combiner (not shown), a fiber optic rotary joint (FORJ), a motion mechanism including a rotational motor and a linear stage, electronic control boards, control buttons and/or an LED panel 1131, and a catheter receptacle 1150.

The catheter 1124 and the handle 1122 that the catheter attaches to are intended to be single-use, sterile components. However the PIU 1130 and a pullback unit (included in the PIU, but not shown) that the catheter interfaces with must be multi-use and unsterile due to costs associated with maintaining or rendering its sterility before use or implementing it as single-use component. The PIU 1130 and pullback unit, when attached to the catheter, must pass into the sterile field in order to facilitate proper catheter deployment control and repositioning. Therefore, a sterile barrier must be introduced between the PIU 1130 with its cable bundle 1106 and the sterile surfaces (e.g., operating table) and catheter handle that it touched in order to avoid contamination of these sterile surfaces.

To that end, the present disclosure provides a novel sterile barrier (a sterile bag or sterile cover) 1200 which extends over the unsterile component(s) of a device requiring passage of said unsterile components into a sterile field. Notably, this novel sterile barrier allows interfacing with the sterile component(s) of the device, while satisfying the need for maintenance of sterility in the sterile field during device deployment and use.

Figure 2:
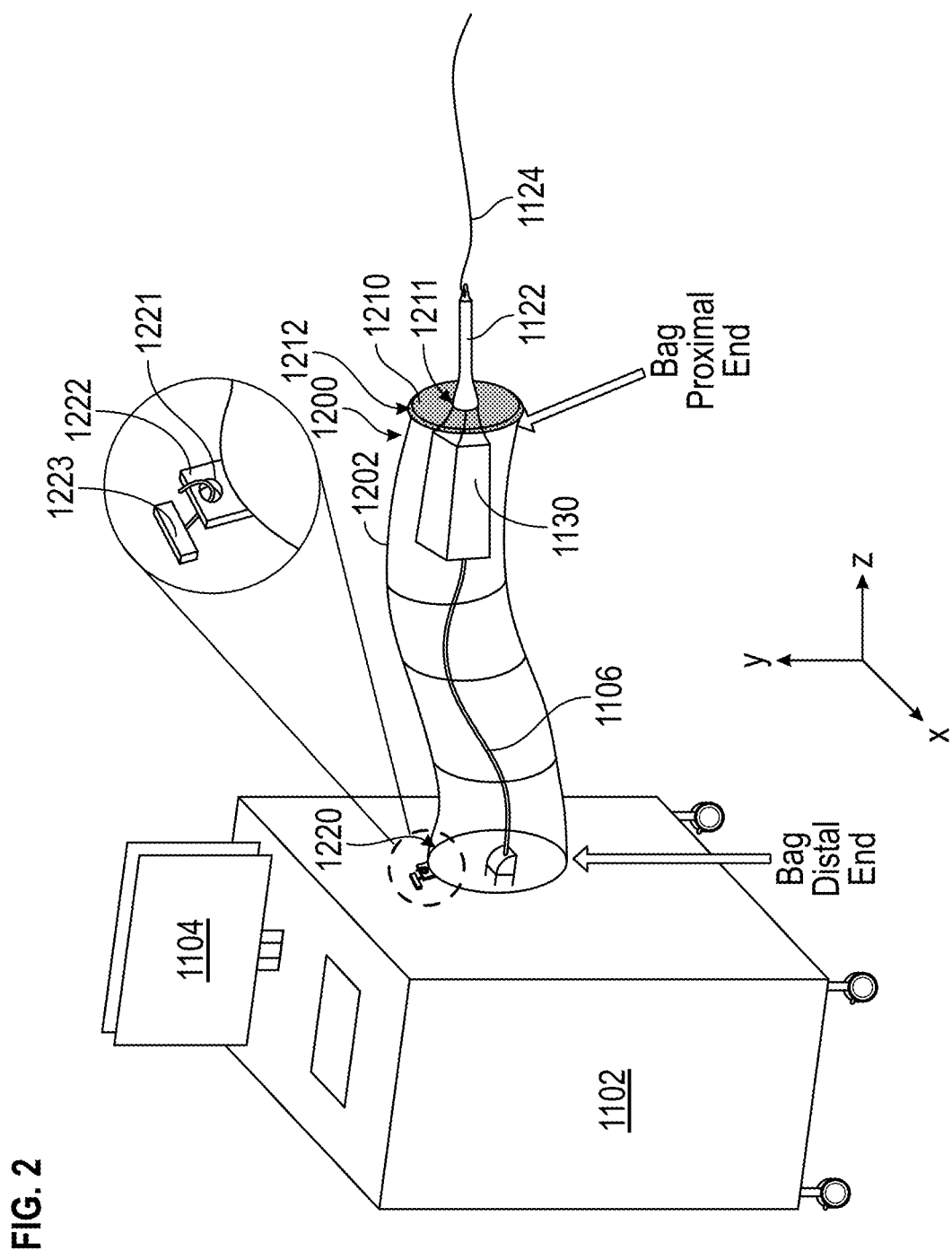
FIG. 2 shows an exemplary embodiment of a sterile cover deployed over non-sterile components of the imaging system.

FIG. 2 shows an exemplary embodiment of the sterile bag 1200 deployed over non-sterile components of the imaging system 1100. In FIG. 2, the bag proximal end and bag distal end are shown in the direction of deployment. As shown in FIG. 2, a sterile bag 1200 includes a flexible body section 1202, a barrier section 1210, and an attaching section 1220. The flexible body section 1202 has a tubular shape extending from a proximal end to a distal end thereof, and having an outer surface, an inner surface, and an open end. As used herein, the term "tubular shape" refers to the flexible body section 1202 being any sterile draping structure having a hollow opening through the center, forming a tube, which can have many different sizes and shapes. For example, the flexible body section 1202 can have a tubular shape long and narrow in some embodiments, while in other embodiments the flexible body section 1202 can have a tubular shape short and wide. Moreover, the term tubular shape does not necessarily limit the flexible body section 1202 to a tubular shape having circular cross-section. In the present disclosure, the flexible body section 1202 can have a tubular shape which is substantially cylindrical, as in the example shown in FIG. 2. In other embodiments, the tubular shape of the flexible body section 1202 can have a rectangular cross-section, so as to have a rectangular tubular shape. In further embodiments, the flexible body section 1202 can have an irregular tubular shape, or the flexible body section 1202 can be open as a flat sheet rolled on one end to form the outer edge of the barrier section 1210, and the other end (attaching section 1220) taped onto the surface of computer cart 1102. In FIG. 2, the flexible body section 1202 is shown as a tube for ease of illustration, but it is not limited to just tubular shapes. Indeed, to facilitate manipulating and engagement/disengagement of sterile components to unsterile components, the flexible body section 1202 may take any shape to even conform to the shape of the medical equipment being covered. In terms of material, the flexible body section 1202 may be made of any suitable, flexible material including textile and/or plastic materials typically used for conventional medical drapes.

The barrier section 1210 includes an outer edge 1212 and a passage 1211 (central opening or through hole). The attaching section 1220 includes one or more attaching components such as an attaching tab 1221 having a thru-hole 1222. In its deployed state, the flexible body section 1202 of the sterile bag (or sterile cover) 1200 has a substantially tubular shape configured to enclose therein non-sterile components including, in the present embodiment, at least the PIU 1130 and cable bundle 1106.

In one embodiment, to reduce the possibility of contact between the sterile bag 1200 and an unsterile surface during or after deployment, the attaching section 1220 may include two or more tabs 1221 each with a small-diameter thru-hole 1221. Additionally, a small hook 1223 for each tab 1221 can be installed around the interface between the unsterile cable bundle 1106 and the main body of the computer cart 1102. The sterile bag 1200, when deployed by an unsterile user, can be held with the hooks 1223 so as to avoid contact between the sterile surface of the bag and the user. When fully deployed, the tabs 1221 can be affixed to the hooks 1223 on the main body of computer cart 1102, thereby temporarily holding the barrier in place while the unsterile component (e.g., PIU 1130) is repositioned. Thus, reducing the possibility of the exterior surface of the sterile bag coming into contact with an unsterile surface outside of the sterile field. FIG. 2 shows the full device with the sterile bag 1200 deployed and affixed to the hook 1223, reducing the possibility of contact between barrier section 1210 and unsterile components (PIU 1130, cable bundle 1106).

Conventionally, the process for sterile bag deployment over the non-sterile components (e.g., PIU 1130, cabling, etc.) is slow because the sterile bag is provided as a separate package and it must be deployed over the PIU before the catheter 1124 is engaged to the PIU. In this process, if the sterile bag comes into contact with non-sterile components, surfaces or users, the sterile bag may lose sterility before even passing into sterile field.

According to the present disclosure, a sterile bag is configured to be preloaded to the disposable catheter handle 1122 in a compact (rolled or pleated) state. In this manner, at the time of deployment process, deployment of the sterile bag can take place at the same time (in parallel) with catheter-to-PIU engagement. To that end, the sterile bag 1200 disclosed herein takes advantage of specifically designed components (sections) which allow the sterile bag to stay compactly attached to the catheter handle prior to deployment and can be quickly deployed during catheter-to-motor engagement.

FIGS. 3A and 3B show an exemplary embodiment of the attaching section 1220 and the barrier section 1210 of the sterile bag 1200. As shown in FIG. 2, the flexible body section 1202 of the sterile bag 1200 has a proximal end and a distal end. At the proximal end, the flexible body section 1202 ends with, or is attached to, the barrier section 1210. At the distal end, the flexible body section 1202 ends with the attaching section 1220. FIG. 3A shows an exemplary embodiment of the barrier section 1210 as seen in the direction along the z axis. The barrier section 1210 has or forms an opening 1211 with a diameter D1 sized to fit a connecting portion 1152 (junction element) of the catheter handle 1122. The connecting portion 1152 (junction element) of the catheter handle 1122 has a diameter "d" approximately the same size of diameter D1 (d≈D1). FIG. 3B shows an exemplary embodiment of the attaching section 1220 also as seen in the direction along the z axis. The attaching section 1220 includes one or more (two in the embodiment of FIG. 3B) attaching tabs 1221, each tab with a thru-hole 1222. The attaching section 1220 in the shape of a ring that has or forms an opening 1225 with a diameter D2 (larger than D1) sized to allow passage therethrough of non-sterile components, such as the PIU 1130 and cable bundle 1106.

Here, a "ring" shaped attaching section 1220 is an optional or alternative embodiment to attach the sterile bag or drape to the system. As noted above with respect to FIG. 2 and mentioned elsewhere in this disclosure, it is sufficient that the sterile bag 1200 includes an attaching section 1220 (attaching component) of any shape or structure which allows secure attachment of the bag's distal end to a fixed surface of the system. To that end, any other attachment structure (e.g., adhesives such as Velcro®) can be used to attach the distal end of the sterile bag 1200 to an unsterile surface (e.g., the surface of the computer cart 1102). The attaching component may include other attaching structures, e.g., fasteners, a clasp, buttons, a zipper or any other suitable mechanism, which can be attached and removed in any suitable manner.

The attaching section 1220 (attaching component) having a ring shape can be made of a rigid polymer, such as nylon; it can be cut from a thin semirigid Mylar sheet, or it can even be made from a piece of sterilized cardboard, etc. Alternatively, a ring shaped attaching section 1220 may be just the open end of a sterile plastic bag. For example, in one embodiment, the simplest implementation of the sterile bag 1200 or sterile cover may be just a long plastic bag with a hole punched in the bottom of the bag through which a connection between the PIU and the catheter handle is made. In this case, the open end of the plastic bag may be reinforced with a piece of rigid or semirigid material to form a ring shaped component around the edge of the bag, and this reinforced edge can be attached to the computer cart of the system. In a further alternative, the open end of a plastic bag can have a hole or more than one hole punched around the edge of the bag, so that the bag can be attached directly to some structure of the system's computer cart.

FIG. 3C shows (for convenience of illustration) the sterile bag 1200 in a predeployed state, where the flexible body section 1202 of the sterile bag 1200 is rolled or creased or folded or pleated to remain compact prior to deployment.

In FIG. 3C, when the sterile bag 1200 is preloaded onto the proximal end of the catheter handle 1122, the opening 1211 of the barrier section 1210 slides over the connecting portion 1152 of the catheter handle 1122 while the attaching section 1220 and flexible body section 1202 are pulled in a direction of axis z (towards the distal end of the catheter handle). The opening 1211 slides over the connecting portion 1152 until the barrier section 1210 abuts against a flange 1122*a* of the catheter handle 1122. To maintain sterility of the catheter handle 1122 and the sterile bag 1200, during the preloading process, at least part of the inner surface 1202*a* of the flexible body section 1202 is exposed outwards. Then, after the sterile bag is preloaded onto the catheter handle 1122, the flexible body section 1202, the barrier section 1210, and the attaching section 1220 are rolled or creased or folded or pleated to remain compact prior to deployment. In other embodiments, the sterile bag 1200 can be deployed onto a non-sterile device without being preloaded onto a sterile device.

FIGS. 4A and 4B show an exemplary process of deploying the preloaded sterile bag 1200 over non-sterile components in parallel to catheter engagement to the PIU. According to the present disclosure, preloading the sterile bag 1200 onto the sterile components of the system offers a significant advantage in usability such that when the mating process between the sterile and unsterile components occurs, any necessary engagement procedure between the two components manifesting as an electrical, mechanical, optical process, etc. can occur in parallel with the deployment of the sterile bag 1200 over the unsterile components (e.g., PIU 1130 and cable bundle 1106). With the expectation that the engagement procedure may take several seconds, preloading the sterile bag on the sterile component eliminates any additional time that would be needed to deploy a non-preloaded bag over the unsterile components followed by the time needed for mating and engagement of the sterile and unsterile components.

FIG. 4A shows a pre-deployment state where the sterile bag 1200 is preloaded at the proximal end of the catheter handle 1122. The general pre-deployment configuration, shown in FIG. 4A, is characterized by the sterile bag 1200 consisting of a rigid or semi-rigid component (barrier section 1210) having a circular surface containing a through-hole 1211 allowing for the junction element (connecting portion 1152) of the sterile component (catheter handle 1122) responsible for mating with the unsterile component (PIU 1130) to pass through. The rigid or semirigid component (barrier section 1210) is connected to the flexible body section 1202 composing the majority of the surface area of the sterile bag 1200 that is pleated or folded in such a way that, the flexible body's surface 1202*a* that will contact the unsterile component's surface when deployed, is facing outward when pre-deployed, while the outward sterile surface 1202*b* faces inward, maintaining its sterility during predeployment. The semirigidity of the barrier section 1210 interfacing with the sterile component's junction element (connecting portion 1152) allows for compression of the barrier section 1210 prior to removing the sterile component and preloaded bag from its packaging while still maintaining the integrity of the sterile bag-junction element connection during predeployment and deployment. The flexible body section 1202 of the sterile bag 1200 can be rolled or pleated or creased or folded with the interior surface 1202*a* facing outward prior to deployment (see FIG. 3C) in order to minimize the probability of contact between the exterior surface 1202*b*, which requires maintenance of sterility, and other unsterile surfaces.

FIG. 4B shows a deployed state of the sterile bag 1200. The preloaded and predeployed sterile bag 1200 can be situated on the junction element (1152) of the sterile component (1122). This is recommended in order to facilitate minimum interference with the sterile component's operation following deployment of the sterile bag 1200 over the unsterile component 1130. Specifically, to ease deployment over the unsterile component, and to secure the sterile barrier's semirigid component between the unsterile and sterile components following mating and engagement, it is advantageous to have the sterile bag 1200 preloaded on the junction element (1152) of the sterile component (1122).

In the event that the sterility of the sterile bag 1200 becomes compromised, e.g., where the bag 1200 may lose its sterility via contact with an unsterile surface following deployment, or the flexible body section 1202 may be punctured, cut, etc., it is proposed that the sterile bag 1200 disclosed herein can be easily removed and replaced, or only replaced. This process can occur before or after the sterile and unsterile components are mated. In the case of removing and replacing the sterile bag prior to components mating and bag deployment, removing the folded/pleated sterile barrier from the junction element (1152) simply involves disengaging the mechanism temporarily attaching it to the element, such as one of those shown in FIG. 3C, and attaching a new folded/pleated sterile barrier using the same mechanism. In the case of replacing the sterile barrier after mating and engagement have taken place, the barrier may be removed via one of the previously mentioned junction element mechanisms before or after deployment without needing to remove the sterile component, and a new folded/pleated sterile barrier may be brought over the sterile component and attached via the same mechanism. Additionally, if the integrity of the barrier to be replaced permits, a new barrier or sterile bag 1200 can simply be affixed and deployed over the previous one without removing the other barrier. This mechanism allows for replacement of the barrier or bag 1200 without removing or replacing the sterile component, thus offering a significant time and cost advantage over having the barrier permanently affixed.

In the case of a compromised sterile component, where the engagement mechanism may fail, or the sterility of the sterile component is compromised, etc., if the sterile barrier or bag 1200 has already been deployed over the unsterile component, the bag or barrier may be left deployed, removed from the sterile component, and affixed to a new sterile component followed by the new sterile component's mating and engagement with the unsterile component. This mechanism allows for replacement of the sterile component without replacing the sterile barrier or bag 1200 already deployed over unsterile components, offering a significant time advantage over having the barrier permanently affixed and needing to redeploy the barrier should the sterile component need to be replaced.

The manner in which the sterile bag 1200 is preloaded onto the catheter handle 1122 is not limited to the usage of a rigid or semirigid barrier section 1210, as described above. The present disclosure also makes use of several other configurations for affixing the rigid or semirigid barrier section 1210 to the junction element (1152) of the catheter handle. The primary configuration can be characterized by the semi-rigid barrier component (barrier section 1210) previously described above with a through-hole 1211 with a diameter D1 slightly smaller than that of the junction element (1152). This allows for holding the barrier section 1210 in place with the elastic force of the barrier component and friction. However other structures and configurations can be used for the barrier section 1210, as shown in FIGS. 5A-5F.

FIG. 5A shows the embodiment of the barrier section 1210, as a separate barrier component made of semi-rigid material having a through hole with a diameter D1, as described above in reference to FIG. 3A. FIG. 5B shows another embodiment of a barrier section 1210, as a barrier component made of a rigid material (higher rigidity than the barrier component of FIG. 5A). The barrier component of FIG. 5B includes a plurality of perforations "p", which serves to provide some flexibility or elasticity to the rigid material. In FIG. 5B, the barrier section 1210 has an inner opening or through-hole 1211 with a diameter marginally smaller than that of the junction element (1152), but with higher rigidity on the side, allowing for higher resistance during preloading and easier translation of the flexible body section in the direction of deployment.

FIG. 5C illustrates a further embodiment of the barrier section 1210 with a 'flower ring' concept, relying on a ring with a diameter D1 smaller than that of the junction element (1152), but with 3 branches 1213 with radii larger than that of the junction element. FIG. 5D illustrates a 'flower ring' concept, relying on a ring with a diameter D1 smaller than that of the junction element (1152), but with 4 branches 1213 with radii larger than that of the junction element. In FIGS. 5C and 5D, the barrier section 1210 has a through-hole with diameter smaller than the junction element (1152), but the material has higher rigidity. In this case, the plurality of branches of the flower ring are flexible, allowing for easier translation in the direction of preloading the bag (see FIG. 3C) and more difficult translation in the direction of bag deployment (see FIG. 4B) over the unsterilized component.

FIGS. 5E and 5F illustrate a further embodiment of a barrier section 1210, shown as a rigid barrier component with trough hole or central opening 1211 having circular cutouts (cut sectors) which are configured to engage with sector protrusions or keys 1153 of the junction element (connecting portion 1152) of the sterile component. These circular cutouts (or cut sectors) around the through hole 1211 function as a locking mechanism 1215. The barrier component 1210 shown in FIGS. 5E and 5F are configured to be paired with junction element (1152) having keys 1153 (shown in FIGS. 6A and 6B). In this embodiment, the rigid barrier component 1210 is first aligned with the keys 1153 so at to match the cut sectors 1215 with the keys 1153, and then rotated in direction R so as to not match the cut sectors with the orientation of the keys 1153 on the junction element (1152), to thereby lock the sterile bag (attached to the barrier component) into place.

The barrier component 1210 can be made of a rigid polymer, such as nylon, punched from a thin semirigid Mylar sheet, or even a piece of sterilized cardboard, etc. Alternatively, it may be just a hole punched in a closed proximal end of a tubular body coupled around it by glue to a rigid flange integral to the catheter handle. In the latter case, the flange could be removed with the handle, but the tubular body may stay over the PIU if needed. For example, in one embodiment, the simplest implementation of the sterile bag or cover may be just a long plastic bag with a hole punched in the bottom of the bag through which a connection between PIU and the catheter handle is made. The hole punched in the bag may be reinforced with a piece or rigid or semirigid material to form the barrier component, as described above, and this bag may be attached to the catheter handle flange with a temporary glue and removed if needed. In other embodiment, the plastic bag having the hole punched in the bottom thereof can be attached directly to the flange 1122a of the catheter handle 1122. In this case the barrier component 1210 has no physical outer edge as it is just the bottom portion of the tubular bag glued to the flange 1122a.

According to the present disclosure, with the sterile bag 1200 being preloaded to the catheter handle 1122 (sterile component), where the unsterile surface of the flexible body of the bag facing outward prior to deployment and allowing for drape deployment to occur simultaneously with mating of the unsterile and sterile components of the device, reducing time need to fully ready the device for use is achieved. Furthermore, in the event that the sterility of the exterior surface of the sterile bag becomes compromised, the method for affixing the barrier component to the sterile component allows for quick removal and replacement of the sterile bag or deployment of another sterile bag over the already deployed sterile bag without requiring removal of the sterile component already connected to the non-sterile component(s). This advantageously reduces the time and cost associated with replacing a damage sterile bag or requiring replacement of the sterile components. Additionally, the sterile component of the device may be replaced without requiring replacement of the sterile barrier and the barrier, if already deployed over the unsterile components of the device, may remain deployed while the sterile component is replaced, again reducing the time and burden that would be required to remove and redeploy a sterile bag if it were permanently affixed to the sterile component.

Another advantage is the provision of attaching tabs at the distal end of the sterile bag allowing for ease of deployment by an unsterile user without compromising the sterility of the sterile bag but also providing for a method of affixing the sterile barrier to a surface so as to avoid contact between the exterior sterile surface and an unsterile surface prior to bringing the barrier into the sterile field. In this regard, although a description has been made of an attaching component being attachable tabs having a thru-hole to engage with hooks, the attachment component is not limited to tabs and corresponding hooks. Any other attachment structure (e.g., adhesives such as Velcro®) can be used to attach the distal end of the sterile bag 1200 to an unsterile surface (e.g., the surface of the computer cart 1102). The attaching component may include other attaching structures, e.g., fasteners, a clasp, buttons, a zipper or any other suitable mechanism, which can be attached and removed in any suitable manner.

The materials for the sterile cover would be selected to provide adequate barrier to prevent through contamination. As such, thin films of non-woven polymers (e.g. polyethylene, polyvinylchloride, polyurethane, polystyrene, polycarbonate, acrylics, silicone rubber, polypropylene, synthetic rubbers, etc.), preferably transparent for ease of use, are commonly employed. In addition, the materials selected should withstand sterilization method(s) selected to be used for the sterile component. For example, for a sterile component containing plastic and requiring Ethylene Oxide (EtO) sterilization method, a 2 mils thick polyethylene film with 10 mils thick Mylar semi-rigid barrier component can be used.

Embodiment(s) of the present disclosure can be modified and/or combined with each other. Moreover, it is understood that numerous modifications may be made without departing from the scope of the disclosed embodiments.

In in the present disclosure, preloading the sterile barrier to the sterile component of a medical equipment system offers a significant advantage in usability such that when the mating process between the sterile and unsterile components occurs, any necessary engagement procedure between the two components manifesting as an electrical, mechanical, or optical process, etc., can occur in parallel with the deployment of the sterile barrier over the unsterile component. With the projection that the engagement procedure may take several seconds, preloading the barrier onto the sterile component eliminates any additional time that would be needed to deploy a non-preloaded barrier over the unsterile component followed by the time needed for mating and engagement of the sterile and unsterile components. The general pre-deployment configuration, shown in FIG. 4A, is characterized by the sterile barrier comprising of a barrier component in the shape of semirigid circular surface containing a through-hole (central opening) allowing for the junction element (connection portion 1152) of the sterile component (catheter handle 1122) responsible for mating with the unsterile component to pass through. The said semirigid barrier component section 1210 connected to the flexible body section 1202 composing the majority of the surface area of the sterile barrier or bag 1200 that is pleated or folded in such a way that, the flexible body's surface 1202a that will contact the unsterile component's surface when deployed, is facing outward when predeployed, while the outward sterile surface 1202b of the flexible body faces inward, thereby maintaining its sterility during predeployment. The semirigidity of the barrier component interfaces with the sterile component's junction element (1152), and allows for compression of the flexible body against the barrier component prior to removing the sterile component and preloaded barrier from its packaging while still maintaining the integrity of the sterile barrier-junction element connection during predeployment and deployment. The barrier can be rolled/pleated with the interior surface facing outward prior to deployment in order to minimize the probability of contact between the exterior surface, which requires maintenance of sterility, and other unsterile surfaces. The predeployed barrier can be situated on the junction element of the sterile component in order to facilitate minimum interference with the sterile component's operation following deployment, ease of deployment over the unsterile component, and to secure the sterile barrier's semirigid component between the unsterile and sterile components following mating and engagement.

Figure 7A:
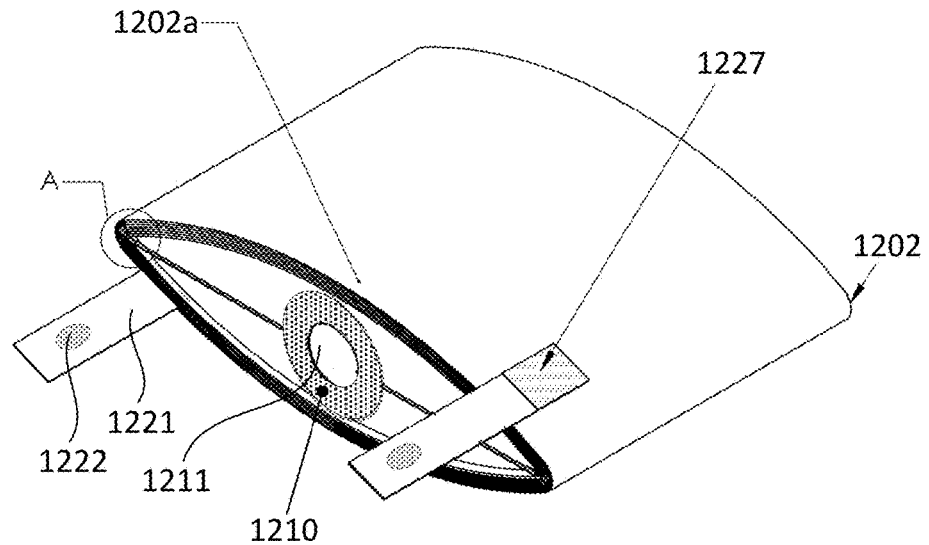
FIG. 7A, FIG. 7B, and FIG. 7C show details of an exemplary sterile cover, drape, or bag 1200 configured to be preloaded to a sterile component or to be attached to an unsterile component of medical equipment.
Figure 7B:
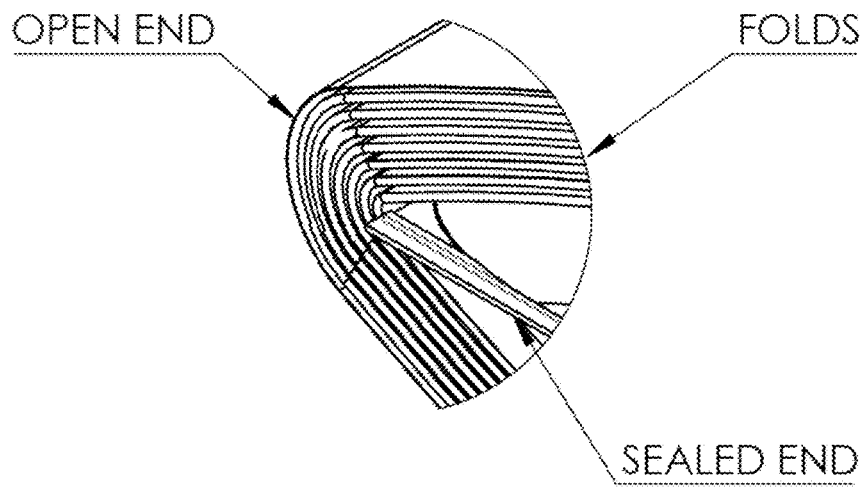
Figure 7C:
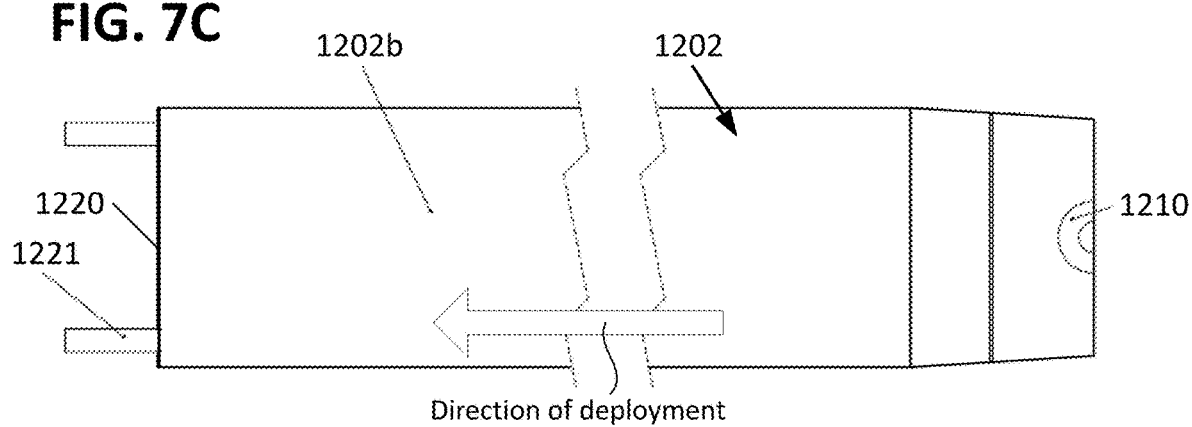

According to another embodiment, the sterile bag 1200 is not preloaded onto the sterile component, but it can be deployed directly onto a non-sterile component in parallel with (or immediately before) the engagement of a sterile component to an unsterile component already covered by the sterile barrier, drape or bag 1200. FIG. 7A, FIG. 7B, and FIG. 7C show details of an exemplary sterile cover, drape, or bag 1200. FIG. 7A shows a perspective view of the sterile cover, drape, or bag 1200 in a preloaded and pre-deployment state. The sterile bag 1200 has a tubular flexible body section 1202, a barrier section 1210, and an attaching section 1220. In its preloaded state, at least part of the non-sterile inner surface 1202a of bag 1200 is exposed outwards. According to the embodiment shown in FIGS. 7A-7C, in the preloaded state, the flexible body section 1202 is rolled or creased or folded or pleated (see detail A) to remain compact prior to deployment. FIG. 7B shows detail A of FIG. 7A as one example of the manner in which the bag 1200 is folded prior to loading and deployment of the bag. Specifically, prior to deployment, the sealed end (barrier section side) and the open end (attaching section side) are at substantially at the same plane, and the body section 1202 is folded with a plurality of z-folds to form a compact package. FIG. 7C shows the deployed state of the sterile bag 1200. To facilitate ease of deployment by a non-sterile user, one or more tabs 1221 are provided around the open end of the body section 1202. The tabs 1221 are attached to the un-sterile inner surface 1202a with an adhesive 1227 (e.g., medical device adhesive or curable material).

In the embodiment shown in FIGS. 7A-7C, the barrier section 1210 has an opening 1211 and an adhesive-backed, semi-rigid ring (see FIG. 3A) meant to provide a means to temporarily affix the bag 1200 to the edge or distal end of the PIU 1130 (see FIGS. 1-2) prior to deployment. Naturally, the adhesive-backed, semi-rigid ring of barrier section 1210 can also provide a means to preload and temporarily affix the bag 1200 to the proximal end of the catheter handle 1122 prior to deployment, as described in the previous embodiments. The drape or bag 1200 is pleated in a z-fold manner prior to deployment, with the interior surface 1202a of the drape facing outwards pre-deployment. Pull tabs 1221 with optional holes 1222 are affixed to the pleated interior surface 1202a of the drape proximal to the semi-rigid ring prior to drape deployment. The tabs 1221 are used for pulling and deploying the bag by placing the bag over the most distal unsterile component, principally the PIU 1130, adhering the interior of the ring to the catheter handle or the edge of the PIU and aligning the opening 1211 around the catheter insertion point, and then unfolding the drape toward the proximal end of the PIU by pulling the pull tabs 1221 in the direction of deployment (see FIG. 7C). Similar to previous embodiments, the diameter D1 of opening 1211 is approximately equal to the diameter "d" of the connection portion 1152 or the sterile component (catheter handle 1122). When fully deployed, the drape or bag 1200 will completely contain the unsterile components of the PIU that pass into the unsterile field and its position will be maintained and not obscure the catheter insertion point on the catheter handle or PIU via the adhesion offered by the semi-rigid ring adhesive or the lock provided by the PIU/catheter handle junction. In addition, to secure the attachment of the deployed sterile barrier or bag 1200 over the unsterile components, the tabs 1221 can be tied, affixed, attached, or otherwise secured to the proximal end of the PIU or to some structure of the console 1110.

In the embodiment of FIGS. 7A-7C, similar to the embodiment of FIGS. 4A-4B, in the event that the sterility of the sterile bag 1200 becomes compromised, e.g., where the bag 1200 may lose its sterility via contact with an unsterile surface following deployment, or the flexible body section 1202 may be punctured, cut, etc., the sterile bag 1200 can be easily removed and replaced, or only replaced, before or after the sterile and unsterile components are mated. In the case of removing and replacing the sterile bag 1200 prior to components mating, removing the folded/pleated sterile bag 1200 from the distal end of the PIU involves detaching the adhesive backed semi-rigid ring 1210 from the catheter handle or the PIU, and attaching a new folded/pleated sterile bag 1200 using the same mechanism. In the case of replacing the compromised sterile barrier after mating and engagement of sterile and unsterile components have taken place, the compromised sterile bag 1200 may be left in place, and a new folded/pleated sterile barrier may be brought over and attached via the same procedure. That is, if the integrity of the new sterile barrier or bag 1200 can be maintained, such new barrier or sterile bag 1200 can simply be affixed and deployed over the previous one without removing the other compromised barrier. This mechanism allows for replacement of the barrier or bag 1200 without removing or replacing the sterile component, thus offering a significant time saving advantage over having the barrier permanently affixed.

An advantage of the sterile barrier disclosed herein is that it provides with the sterile barrier being preloaded to a sterile component by using the rigid or semirigid barrier component. In this manner, the unsterile surface of the barrier can be preloaded facing outward prior to barrier deployment, and during barrier deployment allowing for barrier deployment to simultaneously occur with mating of the unsterile and sterile components of the device, reducing time need to fully ready the device for use. Furthermore, the method for affixing the barrier to the sterile component allows for removal and replacement of the sterile barrier or deployment of another barrier over the barrier already in place without requiring removal of the sterile component of the device should the sterility of exterior surface of the barrier become compromised, reducing the time and cost associated with replacing the barrier requiring replacement of the sterile components. Additionally, the sterile component of the device may be replaced without requiring replacement of the sterile barrier and the barrier, if already deployed over the unsterile components of the device, may remain deployed while the sterile component is replaced, again reducing the time burden that would be required to remove and redeploy a sterile barrier if it were permanently affixed to the sterile component.

An additional advantage of providing tabs 1221 at the distal end of the sterile barrier or bag 1200 is that it allows for ease of deployment of the sterile barrier by an unsterile user without compromising barrier sterility but also providing for a method of affixing the barrier to a surface so as to avoid contact between the exterior sterile surface 1202b and an unsterile component prior to bringing the barrier or bag 1200 into the sterile field.

Definitions

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed. As used herein, the term "sterile" refers to its common medical definition meaning totally clean and substantially free from bacteria or other living microorganisms. Similarly the terms unsterile and non-sterile are interchangeably used to mean not free of living organisms and microorganisms, as in an unsterile medical instrument or a medical operation done in a non-sterile environment.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A sterile drape comprising:
    a flexible body section having a non-sterile inner surface, a sterile outer surface, a proximal end, and a distal end;
    a barrier section made of rigid or semirigid material and having an opening configured to receive therethrough a connecting portion of a sterile component; and
    one or more tabs configured to be tied, affixed, attached, or otherwise secured to a surface of a non-sterile component,
    wherein each of the one or more tabs is attached to the distal end of the flexible body section, and the barrier section is attached to the proximal end of the flexible body section,
    wherein the sterile drape is configured to be preloaded onto the sterile component, by engaging the opening of the barrier section with a connecting portion of the sterile component in a state where the flexible body section is folded or pleated, and causing the barrier section to move with respect to the connecting portion of the sterile component; and
    wherein the flexible body section is deployed over the non-sterile component by unfolding the flexible body section, to thereby at least partially enclose the non-sterile component with the unfolded flexible body section.

2. The sterile drape according to claim 1,
    wherein the sterile drape is preloaded onto the sterile component by pulling from the one or more tabs in a first direction, so that the connecting portion of the sterile component fits tightly through the opening of the barrier section, and the barrier section slides in the first direction with respect to the connecting portion.

3. The sterile drape according to claim 2,
    wherein the flexible body section is configured to be deployed over the non-sterile component by pulling from the one or more tabs in a second direction opposite to the first direction so as to unfold the flexible body section over the non-sterile component.

4. The sterile drape according to claim 3,
    wherein resistance to movement of the barrier section with respect to the connecting portion when the flexible body section is pulled in the second direction is higher than resistance to movement of the barrier section with respect to the connecting portion when the flexible body section is pulled in the first direction.

5. The sterile drape according to claim 1,
    wherein the opening of the barrier section is a circular opening having a diameter D1,
    wherein the sterile component includes a catheter handle, and the connecting portion of the sterile component is a cylindrical catheter connector having a diameter d, and
    wherein the diameter D1 of the circular opening of the barrier section is equal to or smaller than the diameter d of the cylindrical catheter connector.

6. The sterile drape according to claim 1,
    wherein the sterile component is a disposable component, and
    wherein the sterile drape is preloaded onto the disposable component.

7. The sterile drape according to claim 6,
    wherein the non-sterile component is a non-disposable component configured to be mechanically, electrically, and/or optically connected to the disposable component, and
    wherein the sterile drape is deployed over the non-disposable component at the same time as when the non-disposable component is mechanically, electrically, and/or optically connected to the disposable component.

8. The sterile drape according to claim 1,
wherein the non-sterile inner surface and the sterile outer surface opposite to each other, and
wherein the sterile drape is preloaded onto the sterile component with the sterile outer surface facing towards the sterile component and the non-sterile inner surface, facing away from the sterile component.

9. The sterile drape according to claim 8,
wherein the sterile drape is configured to be deployed over the non-sterile component with the non-sterile inner surface facing towards the non-sterile component and the sterile outer surface facing away from the non-sterile component.

10. The sterile drape according to claim 1, wherein the opening of the barrier section is a circular opening having a diameter D1, and the barrier section includes one of (a) a plurality of perforations extending radially away from the diameter D1 of the opening, (b) a plurality of flexible branches arranged in a circular arrangement within the diameter D1 of the opening, and (c) a plurality of cutouts extending radially beyond the diameter D1 of the opening.

11. A method comprising:
providing a sterile drape that includes a flexible body section, a barrier section, and an attaching section, the flexible body section having a non-sterile inner surface, a sterile outer surface, a proximal end, and a distal end; the barrier section made of rigid or semi-rigid material and including an opening, and the attaching section including one or more tabs, wherein the barrier section is attached to the proximal end of the flexible body section, and the one or more tabs are attached to the distal end of flexible body section; and
establishing a connection between a non-sterile component and a sterile component of medical equipment without breaking sterility of the sterile component, wherein the establishing a connection between the non-sterile component and the sterile component, comprises:
preloading the sterile drape in a folded state onto the sterile component by aligning the opening of the barrier section with a connecting portion of the sterile component, and pulling from the one or more tabs in a first direction, such that the connecting portion of the sterile component fits tightly through the opening of the barrier section, and the barrier section slides in the first direction with respect to the connecting portion;
positioning the sterile component preloaded with the sterile drape in close proximity to the non-sterile component; and
deploying the flexible body section over the non-sterile component at the same time as connecting the sterile component and the non-sterile component to each other,
wherein the deploying of the flexible body section over the non-sterile component includes pulling from the one or more tabs in a second direction opposite to the first direction so as to unfold the flexible body section, to thereby at least partially enclose the non-sterile component with the unfolded flexible body section.

12. The method according to claim 11,
wherein the sterile component includes a catheter handle having a flange, and the connecting portion of the sterile component includes a catheter connector, and
wherein preloading the sterile drape onto the sterile component includes inserting the catheter connector of the catheter handle through the opening of the barrier section.

13. The method according to claim 11,
wherein, in the providing step, each of the one or more tabs is provided with at least one hole configured to be tied, affixed, attached, or otherwise secured to a part of the non-sterile component.

14. The method according to claim 11,
wherein the deploying of the flexible body section over the non-sterile component is performed by a non-sterile user.

15. The method according to claim 14,
wherein, during the deploying, the non-sterile user pulls the one of more tabs in the second direction so as to deploy the flexible body section over the non-sterile component in parallel with the attaching of the sterile component to the non-sterile component via the connecting portion.

16. The method according to claim 11, further comprising:
after deployment of the flexible body section over the non-sterile component, removing and replacing or only replacing the barrier section without removing the flexible body section.

17. The method according to claim 11, further comprising:
after deployment of the flexible body section over the non-sterile component, removing and replacing or only replacing the flexible body section without disconnecting the sterile component and the non-sterile component from each other.

* * * * *